US006326143B1

(12) United States Patent
Ørum et al.

(10) Patent No.: US 6,326,143 B1
(45) Date of Patent: *Dec. 4, 2001

(54) METHOD FOR GENERATING MULTIPLE DOUBLE STRANDED NUCLEIC ACIDS

(75) Inventors: Henrik Ørum, Vaerlose; Corina Seeger, Copenhagen K, both of (DK)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/083,123

(22) Filed: May 22, 1998

Related U.S. Application Data

(63) Continuation-in-part of application No. PCT/EP96/05149, filed on Nov. 22, 1996.

(51) Int. Cl.[7] ................................................. C12Q 1/68
(52) U.S. Cl. ..................... 435/6; 435/91.2; 435/91.51; 536/26.74; 536/25.32; 536/25.4
(58) Field of Search .................... 435/91.2, 6, 91.51; 536/26.74, 25.32, 25.4

(56) References Cited

U.S. PATENT DOCUMENTS 4,683,195 * 7/1987 Mullis et al. ........................... 435/6

FOREIGN PATENT DOCUMENTS

| 0 379 369 | 7/1990 | (EP) | ................................ C12Q/1/68 |
| 0 469 755 | 2/1992 | (EP) | ................................ C12P/19/34 |
| 0 549 107 | 6/1993 | (EP) | ................................ C12Q/1/68 |

OTHER PUBLICATIONS

International Publication No. WO 93/12245 published Jun. 24, 1993.

\* cited by examiner

*Primary Examiner*—W. Gary Jones
*Assistant Examiner*—Joyce Tung
(74) *Attorney, Agent, or Firm*—Arent Fox Kintner Plotkin & Kahn

(57) ABSTRACT

The present invention concerns a method for generating multiple double stranded nucleic acids by (a) elongating a primer molecule comprising a nucleobase sequence B' by using one or more nucleotide(s) and a target nucleic acid T that acts as a template for the elongation of said primer such that the elongation product E formed is capable of acting as a template for the elongation of a further primer molecule containing the nucleobase sequence B'; (b) separating the target nucleic acid T from said elongation product E; (c) using said elongation product E as a template for the elongation of a further primer molecule yielding an elongation product E'; and (d) repeating the steps of elongating primer molecules and of separating said elongation products a sufficient number of times to achieve the desired amount of double stranded nucleic acid.

20 Claims, 13 Drawing Sheets

Fig.5A

→ ELONGATE
→ DENATURE
→ HYBRIDIZE
→ ELONGATE
→ DENATURE 1x
5' - $Y_1$ $Y_2$ $Y_3$ $Y_4$ ..... $Y_{m-1}$ $Y_m$ $X_1$ $X_2$ $X_3$ $X_4$ ..... $X_{n-1}$ $X_n$ - 3'  TARGET 7x
5' - $X'_n$ $X'_{n-1}$ ..... $X'_4$ $X'_3$ $X'_2$ $X'_1$ I I I I I ..... I I - 3' ELONGATES
$E + E'$

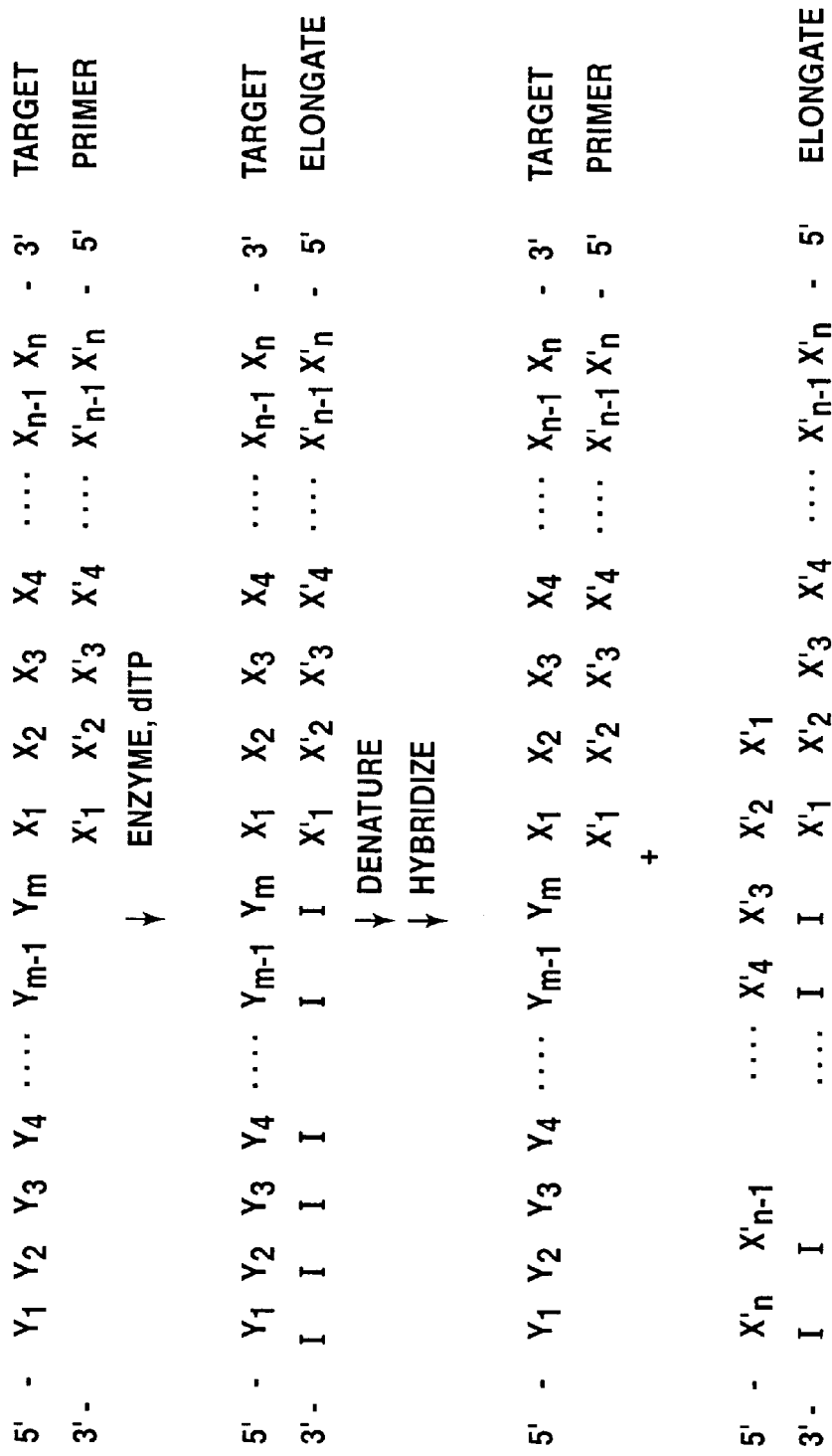

Fig.6A

→ ELONGATE
→ DENATURE
→ HYBRIDIZE
→ ELONGATE
→ DENATURE 1x
5' - $Y_1$ $Y_2$ $Y_3$ $Y_4$ .... $Y_{m-1}$ $Y_m$ $X_1$ $X_2$ $X_3$ $X_4$ .... $X_{n-1}$ $X_n$ - 3' TARGET 7x
5' - $X'_n$ $X'_{n-1}$ .... $X'_4$ $X'_3$ $X'_2$ $X'_1$ I I I I .... I I - 3' ELONGATE

Figure 8A

→ Elongate
→ Denature
→ Hybridize
→ Elongate
→ Denature 1x  5' - C C C C C ····· C C C C C I I I I I ····· I I I I I - 3'  Target T 7x  5' - C C C C C ····· C C C C C G I I I I I ····· I I I I I - 3'  Target T
                                                                    Elongate E further cycling increases amount of Elongate E

SEQUENCE LISTING

<160> NUMBER OF SEQ ID NOS: 8

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: made by humans
<220> FEATURE:

```
<220> FEATURE:
<221> NAME/KEY: modified_base
<222> LOCATION: (31)..(60)
<223> OTHER INFORMATION: n is deoxyinosine, i.e. i

<400> SEQUENCE: 1
cccccccccc cccccccccc cccccccccc nnnnnnnnnn nnnnnnnnnn nnnnnnnnnn      60

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: made by
      humans

<400> SEQUENCE: 2
cccccccccc cccccccccc cccccccccc                                      30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: made by
      humans

<400> SEQUENCE: 3
tttttttttt tttttttttt tttttttttt                                      30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: made by
      humans

<400> SEQUENCE: 4
cccccccccc cccccccccc cccccccccc g                                    31

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: made by
      humans

<400> SEQUENCE: 5
cccccccccc cccccccccc cccccccccc gg                                   32

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: made by
      humans
<220> FEATURE:
<221> NAME/KEY: modified_base
<222> LOCATION: (1)..(30)
<223> OTHER INFORMATION: n is deoxyinosine, i.e. i

<400> SEQUENCE: 6
nnnnnnnnnn nnnnnnnnnn nnnnnnnnnn                                      30
```

```
<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: made by
      humans

<400> SEQUENCE: 7
aaaaaaaaaa aaaaaaaaaa aaaaaaaaaa                                      30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: made by
      humans

<400> SEQUENCE: 8
gggggggggg gggggggggg gggggggggg                                      30
```

METHOD FOR GENERATING MULTIPLE DOUBLE STRANDED NUCLEIC ACIDS

CROSS REFERENCE TO RELATED APPLICATION

This application is a continuation-in part of International Application PCT/EP96/05149, filed Nov. 22, 1996, and designating the U.S.
Method for Generating Multiple Double Stranded Nucleic Acids The present invention is directed to a method for generating multiple double stranded nucleic acids and to a method for the determination of an analyte by using the generated multiple double stranded nucleic acids.

BACKGROUND OF THE INVENTION

The determination of analytes in samples plays an important role in either environmental or human diagnostics analysis. The infection or pollution of samples by substances coming from the environment is becoming a major focus of the industry. Because many of the substances are present in samples in very low amounts, the methods for the analysis must be very sensitive. This is especially true for immunological determinations or analyses based on the occurrence of nucleic acids.

The first increase in sensitivity to be achieved in nucleic acid assays was realised by the possibility to amplify the amount of analyte nucleic acid in a sample. This has made possible the determination of even very low amounts of nucleic acids present in a sample. One example of a method for the amplification of analyte nucleic acids in a sample is the so-called polymerase chain reaction which is described in detail in U.S. Pat. No. 4,683,202. This method uses two primers chosen such that the sequence of the first primer is complementary to a region of the target nucleic acid to be amplified and the sequence of the second primer is homologous to a sequence on the target nucleic acid such that the elongation product of one primer can be used as a template for the elongation of the other primer. This method yields multiple copies of the nucleic acid to be determined.

As a further development of this method in EP-A 0 379 369 there is described a method for converting an analyte polynucleotide into a polynucleotide having at one terminus a nucleobase sequence which is complementary to the sequence at the other terminus. This newly constructed polynucleotide containing a fragment of the analyte nucleic acid is capable of being amplified using only one primer sequence. This procedure, however, has the disadvantage that the termini of the nucleic acid produced can hybridise to each other and therefore can prevent annealing of the primer. Therefore the amplification is not very effective. Further, the preparation of the amplifyable intermediate product requires the use of two different primer sequences and hence knowledge of two different sequences in the nucleic acid to be determined or amplified.

Therefore, it is the object of the present invention to provide the art with a method for generating multiple double stranded nucleic acids which can be used to determine analytes, where only one primer sequence is used.

SUMMARY OF THE INVENTION

Subject of the present invention is therefore a method for generating multiple double stranded nucleic acids by a. elongating a primer molecule comprising a nucleobase sequence B' by using one or more nucleotide(s) and a target nucleic acid T that acts as a template for the elongation of said primer such that the elongation product E formed is capable of acting as a template for the elongation of a further primer molecule containing the nucleobase sequence B';

b. separating the target nucleic acid T from said elongation product E, c. using said elongation product E as a template for the elongation of a further primer molecule yielding an elongation product E', d. repeating the steps of elongating primer molecules and of separating said elongation products a sufficient number of times to achieve the desired amount of double stranded nucleic acid.

A further subject of the invention is a method for the determination of an analyte using this method, especially binding to said analyte a target nucleic acid T having a region comprising an analyte-specific region A and a region comprising an analyte-nonspecific nucleobase containing sequence B;

hybridising to said target nucleic acid a primer comprising a nucleobase sequence B' complementary to said sequence B;

elongating said primer using said target nucleic acid as a template to form a first elongation product E by the covalent attachment of one or more nucleotides to said primer;

determining the occurrence of said elongation product as a measure of the presence or amount of the analyte.

DETAILED DESCRIPTION OF THE INVENTION

According to the present invention, a method for generating multiple double stranded nucleic acids is a method for the creation of a large number of identical double-stranded nucleic acids. This method will comprise, but not necessarily essentially consist of, an amplification of these double stranded nucleic acids. The amplification may be linear, but may preferably be perfectly or imperfectly exponential. Perfectly exponential would be an amplification wherein the number of nucleic acids created in n amplification steps amounts to $2^n$, whereas in an imperfect exponential amplification this theoretical amplification factor will not be achieved. The double stranded nucleic acids generated can be subject to further processing steps like chemical modification or physical treatment, like strand separation yielding single stranded nucleic acids.

A primer according to the present invention is a molecule comprising a nucleobase sequence B' which has an affinity to a nucleobase sequence B contained within a target nucleic acid and is capable to be elongated by nucleotide(s) at an elongatable end. Preferably, the nucleobase sequence B' of the primer is substantially complementary to a nucleobase sequence B in the target nucleic acid. Preferably, the primer has such a specificity for the target nucleic acid or the nucleobase sequence B such that it does not hybridise under the conditions chosen to nucleic acids not intended to be used as target for generating multiple double stranded nucleic acids. The primer according to the present invention is preferably a nucleic acid, for example DNA or RNA, DNA being preferred. The primer can act as substrate for attachment of one or more nucleotides The primer has a 3'-terminal hydroxyl group to which mononucleotides can be attached enzymatically using the protruding end of the target nucleic acid as a template, thus forming an elongation product of the primer. In the following, the end of the primer intended to be elongated is named elongatable end of the primer. Primers are generally used in large excess over the target nucleic acid.

In a special embodiment the primer contains a stretch of at least 10 nt of continously connected nucleotides bearing the same nucleobase, preferably a pyrimidine nucleobase like T or C, most preferred cytosine. Most preferably, this stretch is located within sequence B'. At the elongatable end of the primer the primer may contain one or more nucleotides which differs from the nucleotides in the above mentioned stretch and improves the selectivity of a the binding of the primer to the nucleobase sequence B of the target nucleic acid T. In a preferred embodiment the primer contains a stretch of identical bases of preferably at least ten identical bases in consecutive order and, in the direction of the elongation, three or less bases differing from the before mentioned bases. Preferably only two or one such base is attached to this terminus of the stretch. Preferred bases at the elongatable terminus of the primer are bases which can form base pairing with the before mentioned stretch of identical bases in the primer. However, the number of these bases is less than the number useful to produce stable intra-probe structures. The primer can have attached further moieties, provided that they do not make impossible the hybridisation of the primer to the target and subsequent elongation. Especially, moieties possibly attached to the primer comprise labelling groups. The sequence B' is predetermined and chosen such that it fits to the corresponding stretch of nucleobases in the target nucleic acid.

A nucleobase sequence according to the present invention is composed of naturally or non-naturally occurring nucleobases linked together by a backbone, for example, a sugar-phosphate backbone as in usual nucleic acids. The nucleobase sequence, for example, determines the specificity with which a primer binds to a target nucleic acid. For achieving a certain specificity it may be appropriate to chose the nucleobase sequence to be longer than 15 nucleotides (nt), preferably between 16 and 30 nt.

A target nucleic acid is a nucleic acid which is contained within or isolated from a sample or is produced in a pre-step or is added to the sample in a defined amount. Preferably the target nucleic acid is not a naturally occurring nucleic acid but a construct being composed of components adapted for a specific use of the target nuceic acid. In a more preferred case the target nucleic acid is composed of components allowing the determination of an analyte in a sample. This embodiment of the invention is described in detail later. The target nucleic acid can be discriminated from other ingredients of the reaction mixture, for example by nucleobase sequence B. The target nucleic acid according to the present invention is the starting compound for the method for generating multiple nucleic acids. The target nucleic acid contains two or more parts, each part containing a nucleobase sequence. The two essential nucleobase sequences of the target nucleic acid are named sequence I and sequence B. Sequence I is used as a template sequence in the present invention. The sequence B in the target nucleic acid to which nucleobase sequence B' of the primer hybridises may be located at any position on the target nucleic acid. However, it must be recognised that the target nucleic acid is protruding on at least one side of the nucleobase sequence B' when the primer is hybridised to the target, such that the elongatable end of the primer faces to the protruding end. Preferably, the protruding end is near to the 3'-terminus of the primer. This protruding end of the target nucleic acid is that end of sequence B to which sequence I is attached. At the other end of sequence B other moieties or nucleobase sequences may be attached or may not be attached. The sequences I and B are linked such that elongation of the primer using sequence I as a template is possible. Therefore, in most cases the natural linkage between mononucleotide moieties of a nucleic acid is preferred.

It is preferred that sequence B and its position in the target nucleic acid is predefined and unique. However, it is not excluded that there may be more than one predefined and independent positions in the target nucleic acid to which the primer can bind.

The sequences I and B have preferably a length that allows the specificity necessary for the intended use of the method of the invention. If no high specificity or selectivity is necessary, these sequences can have a low number of nucleotides in length, e.g. eight or more nucleotides. In the case that the reaction mixture contains other nucleic acids that could destroy the required specificity, it might be appropriate to choose the sequences I and B longer than 15 nt, more preferably 15 to 30 nt. The sequence B is designed such that the nucleobase sequence B' of the primer can hybridize to the target nucleic acid at this sequence. Therefore it contains sufficient complementarity to the primer sequence B'. In most cases it may be required that the complementarity at that end of sequence B' at which elongation of the primer is intended to the corresponding part of sequence B is perfect. Sequence B is preferably an analyte non-specific sequence and is not designed and intended to bind by direct base pairing to the analyte or any substances in the reaction mixture, for example a sample possibly interfering with the specificity of the generation or determination. This sequence B contains preferably a stretch of at least 10 nt of continuously connected nucleotides bearing the same nucleobase. It may have a different base located at the position directly adjacent to this stretch in the 5'-direction. For example, sequence B can consist of oligo dA or oligo dG or oligo dC or oligo dT. Preferably, it consists of oligo purine, especially oligo dG or oligo dI. In a preferred case the length of sequence B is 6, 4 or 2 nucleotides longer than the length of sequence I. The reasons for this will be explained later.

The nucleotide used for the elongation of the primer in the present invention may be a mononucleotide, an oligonucleotide or polynucleotide. Preferably, the nucleotide is a mononucleotide, especially a mononucleosidetriphosphate, most preferred a monodeoxyribonucleoside triphosphate (dNTP). In this case, it is preferred that the primer is elongated by at least 10, preferably between 11 and 30 nucleotides in the elongation step. Usually the elongation will terminate as soon as the end of the protruding part (of sequence I) of the target nucleic acid is reached.

Elongation of the probe, when hybridised to the target nucleic acid is dependent on the kind of nucleotides used. On the one hand, elongation can be achieved by chemical means, when the probe and the nucleotide have chemical groups capable of reacting with each other, or by enzymatic means. Enzymatic elongation is the preferred case. Enzymes being capable of elongating a probe using a target nucleic acid as a template are generally known. For example, DNA-polymerases are capable to elongate primers by sequential addition of dNTPs to their 3'-end. Preferred polymerases are, for example, available from *E. coli* or other bacteria and viruses. Thermostable enzymes are also available.

Another group of enzymes useful for an embodiment of the invention are ligases which catalyse the covalent joining of two oligonucleotides. Then one of the oligonucleotides is acting as the primer, the other acting as the nucleotide.

A template according to the invention is a nucleic acid containing a rimer hybridization part and a template part.

A template part of a nucleic acid according to the invention has a nucleobase sequence that can act as a substrate for making a primer elongation product when the primer is hybridized to a location adjoining the template sequence under conditions allowing elongation. Preferably it will have a predetermined, defined or undefined sequence. The sequence must allow elongation of a primer and must therefore have a sufficient length. The template sequence may incorporate a sequence that is specific for a specific compound, for example, a nucleic acid to be determined. The elongation of the primer yields an elongation or extension product of the primer such that the primer contains more bases at its elongatable end after elongation than before. Preferably the extension starts at the 3'-terminus of the primer and terminates at the end of the template sequence. The first template sequence used in the present invention is part I of the target nucleic acid.

The method for the generation of multiple nucleic acids of the present invention works with a sequence of steps. After any preparational steps that might be necessary to create a sample wherein the target nculeic acid is accessible to the reagent used in the invention the first essential step of the present invention is the hybridization of a primer molecule to the nucleobase sequence B of the target nucleic acid T. The conditions usefil for hybridization depend e.g. upon the length of the primer, the degree of compiementarity and the base composition of the primers. However, such hybridization conditions are generally known to a man skilled in the art. Especially such conditions can be choosen following the disclosure of Molecular Cloning, Editor: J. Sambrook et al., Cold Spring Harbor 1989.

In a subsequent step the primer molecule hybridized to the target nucleic acid is subjected to conditions suitable for elongation of the primer molecule using nucleobase sequence I of the target nucleic acid as a template for the elongation of this primer. The elongation conditions of course depent upon the kind of elongation used. Generally the conditions for the most suitable elongation reactions, for example the DNA polymerase catalyzed elongation of primers by sequencial addition of dNTPs is described in Molecular Cloning (see above). Some helpful hints are also given in U.S. Pat. No. 4,683,202. The temperature during the elongation step will be choosen such that the primer remains hybridized to the target nucleic acid but in a way that it allows optimal elongation. In the case of enzymatic elongation, the temperature should be in the vicinity of the temperature which is optimum for enzyme activity. Otherwise the velocity of elongation may be not optimal. Of the polymerases useful in the present invention, DNA-dependent DNA-polymerases are especially preferred. Such enzymes are available from *E. coli*, T7, etc, for example.

The elongation product E formed from the first elongation is the elongated primer comprising the primer sequence and the attached nucleotide(s). In most cases therefore the elongation product will extend relative to the target nucleic acid over the sequence B and the sequence I.

A second essential step in the method of the present invention is the release of the target nucleic acid T from the elongation product E in a way that the elongation product E and, most preferably, also the target nucleic acid T is accessible to hybridization with a further primer molecule.

The separation of a template from the elongation product can take place by known methods, for example, by chemicals, like alkali, or by physicals means, like heating above the melting point of the hybrid formed from the template nucleic acid and the elongation product. Preferably the separation takes place by heat. The temperature will depent upon the length of the elongation product and the complementarity and base composition of the elongation product and the primers. General outlines are also disclosed in Molecular Cloning (see above).

In a third essential step of the method the elongation product E is used as a template for the elongation of a further primer molecule. This means that the further primer molecule hybridizes to a part of the elongation product which was newly created by attachment of nucleotides to the first primer molecule. Then a nucleobase sequence contained in the former primer molecule will act as the actual template for the elongation of the further primer molecule. If sequence I and therefore the newly created sequence is longer than sequence B' of the primer, then it is not required that the primer hybridizes to the elongation product such that a part of the primer molecule containing the elongatable end hybridizes to nucleobases of sequence B' of the former primer molecule. In a preferred case, however, sequence I is shorter than sequence B and sequence B', and therefore there will be an overlap of bases steming from the former primer molecule and the new primer molecule in the hybrid formed from the elongation product and the further primer molecule. The same considerations apply as above. This again means that the temperature should be below the melting temperature of the hybrid formed from the elongation product and the primer. The site of the elongation product E to which the primer molecule hybridizes is choosen such that at the elongatable terminus of the primer there is a sufficient length of a nucleobase sequence protruding on the elongation product that can serve as a template for the elongation of the further primer molecule. The template part in this step of the method is therefore in most cases the part of the elongation product steming from the first primer molecule, while the primer hybridization side will contain at least a part of the sequence formed by attachment of nucleotide(s). The elongation product formed in this third step is termed E'.

While in the first step of the method of the present invention the first molecule of primer is used, in the second step there is used a further molecule of said primer. It is important to understand that the method of the present invention enables the generation of multiple nucleic acids by only one kind of primer. If severaltiegions of a target nucleic acid shall be made subject for making multiple nucleic acids, of course, it may be required to use primers of a different sequence for the other region(s).

In a preferred embodiment of the invention the length of the sequences I and B are choosen such that the primer molecule when hybridized to the elongation product spans a sequence newly formed by attachment of nucleotides and a part of sequence B'. This embodiment is shown in FIG. 2B. The overlap should be not more than 6, preferably 4 or less and most preferred 2 nt. The reason for this embodiment is that the primer hybridization sites can be used to create elongation products of a specific length, even if only one kind of nucleotide is attached in the elongation step or/and primers containing substantially only one kind of nucleotides. A more preferred embodiment will be given below.

The method of the present invention can be realized by mixing the necessary reagents together and then use a temperature profile that allows the conduction of the steps of the present invention. Result of the steps mentioned above are a duplex of elongation product E and elongation product E', and if the target nucleic acid was not destroyed during the preceeding steps, a hybrid of the target nucleic acid and a further molecule of the elongation product E. In the preferred case, the elongation product E and elongation product E' have essentially the same nucleobase sequence. This is especially true, when only one kind of nucleotide is attached during the elongation. This fact reduces the complexity of the reaction considerably. These hybrids can be processed in any desired step. If the amount of nucleic acids required is already reached, the method of the invention may be stopped at this point. Then the hybrids can be subjected to any desired further reaction or isolation, determination etc. This may or may not include separation of the strands of the duplexes and/or hybridization of further nucleic acids to the products.

However, in a preferred case the amount of the nucleic acids created, e.g. of the elongation products E or E', is further increased. Similar to the cycling in the polymerase chain reaction of U.S. Pat. No. 4,683,202 the products (elongation products) or/and the starting compounds (target nuclec acid ) of the previous steps can be used as substrates in the next cycle of steps thereby increasing the number of nucleic acids (elongation products) generated. Each cycle of steps will therefore include a step of hybridising the primer to a nucleic acid containing, a step of elongating the primer and a step of separating the former template from the elongation product. In order to illustrate the present invention, it might be added that in every cycle of reactions according to the invention a new target nucleic acid T is produced by forming an elongation product so every cycle can be considered to be starting the method of the invention again. According to the intended use of the method of the present invention, the cycling can stop at any of these cycles. The method will generally be finished, when the desired amount of double stranded nucleic acids are generated. In general, the number of cycles of steps will be between 10 and 50, preferably of between 15 and 30. In another definition, the number of double stranded nucleic acids generated should be more than 9, preferably more than 100.

One of the characteristics of the polymerase chain reaction is that the cycling is achieved by just repeating the temperature protocol a sufficient number of times. In the present case after step c) the hybrids formed from the elongation products and the starting compound is denatured to allow further hybridization of a further primer molecule to the starting compound as well as each of the elongation products (E and E'). In each cycle the number of copies of the elongation products will be increased.

The method according to the invention can stop at any step. For example, if single stranded nucleic acids are desired instead of double stranded nucleic acids, it is possible to stop the cycling with a step separating the double stranded nucleic acids formed from the elongation products and/or the staring compounds (target nucleic acids). The same holds true if a hybrid formed from a primer molecule and an elongation product is the intended product of the procedure. Then it is simply possible to destroy the elongating activity (e.g. enzymatic activity) while maintaining the hybridization conditions.

One preferred aspect of the present invention is the use of nucleotides, most preferred dNTPs containing a promiscuous base for attachment to the primer. The promiscuous base is defined according to the present invention to be capable of base pairing with each of the nucleobases, adenine, guanine, cytosine and thymine. While the affinity to some of the bases may be higher than to others, a promiscuous base is principally able to base pair with all of them. Such a promiscuous base is, for example, inosine. So, the use of one kind of mononucleosidetriphosphate allows the primer to be elongated irrespective of the kind of nucleotides in the template. Since inosine makes better basepainng with cytosine than with adenosine and still better than with thymine and guanine, the method will presumably work the best the more cytosine is contained within the template sequence. A result of the elongation of the primer with inosine triphosphates exclusively is that the sequence-specific information in the target sequence is not maintained in the primer elongation product. According to the invention, however, it is possible to maintain some sequence specific information in the elongation product by incorporating a certain amount of either dATP, dGTP, dCTP or dTTP in the elongation reaction. Typically at least 30% of the bases present in the nucleotide are promiscuous bases, more preferable more than 80% and most preferable 100% or all of these bases. Strictly speaking, this aspect of the present invention does not yield an amplification of an original target nucleic sequence, while it may be considered as amplification of a sequence created from the target sequence. A further consequence of the embodiment using one promiscuous base is that the nucleobase sequence of elongation products E and E' are essentially the same. Further they may hybridize with each other.

The use of a promiscuous base in the nucleotides used for elongation of the primer gives to the duplex formed between the target nucleic acid and the elongation product a melting temperature which is considerably below the melting temperature of hybrids having A/T or A/U and C/G base pairs. This leaves the present invention with the advantage that it is possible to denature the hybrids at relatively low temperatures, preferably below 55° C., most preferably below 45° C., for target or template nucleic acids of a length of about 30 nt. The denaturation step is usually the step in an amplification procedure requiring the highest temperature. Therefore, it is possible according to the present invention to provide the art with a method for amplifying nucleic acid sequences using thermocycles including the steps primer hybridisation, primer extension and thermal denaturation, not comprising a temperature exceeding 55° C., preferably not exceeding 45° C.

Preferred embodiments of this method for generating multiple double stranded nucleic acids are described below in connection with the detained description of the drawings.

This method for generating multiple double stranded nucleic acids can be used very advantageously for the determination of analytes. The method for the determination of an analyte according to the invention is principally defined by the following steps:

Binding a target nucleic acid T to the analyte;

Optionally separating the analyte bound to the target nucleic acid from the remaining sample;

Subjecting the target nucleic acid to the above mentioned method for generating multiple double stranded nucleic acids and determining the occurrence of the elongation products as a measure of the presence or amount of the analyte.

An analyte in these methods can be any molecule capable of being recognised by a probe, preferably immunologically active analytes, like antibodies, antigens or haptens, or nucleic acids or nucleic acids analogues. The determination of nucleic acids is a preferred embodiment of the determination method of the invention.

The analyte to be determined can be a component of a sample, like a body fluid or a fluid derived therefrom. In case of nucleic acids, usually any samples are subject to preceeding steps for releasing the nucleic acids possibly contained within cells. The analyte nucleic acid can therefore be of any origin, especially of bacterial or viral origin. The analyte nucleic acid can especially be a ribonucleic acid or a deoxyribonucleic acid.

A further subject of the invention is therefore a method for the determination of an analyte by binding to said analyte a target nucleic acid T having a region comprising an analyte-specific region A and a region comprising an analyte-non specific domain containing a nucleobase sequence B; hybridising to said target nucleic acid a primer comprising a nucleobase containing sequence B' complementary to said sequence B; elongating said primer using said target nucleic acid as a template to form a first elongation product E by the covalent attachment of one or more nucleotides to said probe and determining the occurrence of said elongation product as a measure of the presence or amount of the analyte.

Compared to the method for generating multiple double stranded nucleic acids as described above the method for the determination of the analyte requires the target nucleic acid to have an analyte-recognising region A. This region A in the target nucleic acid is a moiety recognising the analyte in a specific way, e.g. only the analyte to be determined is recognised under the conditions applied. Therefore this region A can be a region recognising an epitope or a nucleobase sequence of the analyte, for example, an antibody moiety or a nucleobase sequence complementary to a part of the analyte nucleobase sequence.

Dependent on the kind of analyte-specific region (immunologically active site, nucleobase sequence etc.) the analyte specific region may or may not be located within the sequence I of the target nucleic acid T. The main consideration on where region A is located is whether the elongation of the primer using sequence I as a template is still possible.

The analyte-specific region A and the sequence B can be linked covalently or non-covalently, but are preferably linked covalently. In the special case, wherein A and B are nucleotide sequences it is preferred that the 5'-terminus of A is linked to the 3'-terminus of B or the 3'-terminus of A is linked to the 5'-terminus of B.

A and B can be linked directly or via an intermediate moiety. Such an intermediate moiety can be a further nucleobase sequence of a length of more than 10 nucleotides, preferably between 12 and 20 nt. This nucleotide sequence is preferably not specific to the analyte. Therefore it can be even a nucleotide sequence consisting of identical base units, for example, oligodA, oligodG, oligodC or oligodT. Preferably this intermediate sequence is designed to be capable to act as a template for the elongation of a primer hybridized to sequence B, and most preferably is sequence I. In the most preferred case of the determination of a nucleic acid the target nucleic acid T is a functional oligonucleotide containing in this order (5'-) the analyte-specific sequence A, the intermediate template sequence L and the analyte-non specific sequence B(-3').

The binding of the target nucleic acid to the analyte takes place under conditions which allow the analyte recognising region A to bind to the analyte. Preferred interactions are specific interactions like in immunological reactions or nucleobase pairing. The conditions under which these bindings occur are known to a man skilled in the art.

The optional step of separating the analyte bound target nucleic acid from the remaining sample is mostly helpful in increasing the specificity of the determination. This separation is preferably performed by immobilizing the complex on a solid phase, preferably by using an analyte specific solid phase. Analyte specific solid phases are for example solid phases which have attached their two moieties recognising the analyte, for example antibodies against the analyte. The conditions for binding the complex to the solid phase may be applied as in usual immunochemical determinations, like the conditions described in U.S. Pat. No. 4,624,930. By removing the remaining liquid from the solid phase, the excess of target nucleic acid is washed away together with other disturbing substances.

Some preferred embodiments of this method are described below in connection with the detained description of the drawings.

The method for the determination of an analyte is finalized by determining the occurence of said elongation product as a measure of the presence or amount of the analyte. The occurence of the elongation product can be determined directly or indirectly. All methods generally usefull for the determination of nucleic acids are applyable for the method for the determination of the elongation product. In almost every case the occurence of the elongation product will be made dependent on the occurence of a labelled moiety. There are two especially favoured ways of determining the elongation products.

In a first preferred embodiment the elongation product is hybridized to a labelled probe, e.g. a nucleic acid which in itself is capable of being determined, e.g by having attached a detectable label, like a fluorescent moiety or a moiety being capable of being attached to a detectable moiety, e.g. biotin or digoxigenin (for example according to U.S. Pat. No. 5,344,757). Generally the amount or presence of an hybrid formed from the elongation product and this probe is determined. It may be advantageous to use the probe in an excess amount over the elongation product and separate off the amount of probe not bound to the elongation product. This can be made in a simple way by using a further probe designed to bind the elongation product at a different site than the probe. The general format can follow the known "sandwich hybridization assay formate". One suitable method is described in EP-A-0 079 139. This method can be applied by chosing the elongation product as the nucleic acid to be determined.

A further advantageouses method for determining the amount of elongation product is to incorporate a label into the elongation product. It is especially convenient to label the elongation product during its generation, most preferably by using labelled nucleotides for attachment. It is understood that not all nucleotides incorporated must be labelled in any case. In this case the determination of the elongation product can be made simply by separating off the excess of labelled nucleotide, e.g. by capturing the labelled elongation product on a solid phase and removing the excess nucleotides with a solution. This procedure can follow the general disclosure of EP-B-0 237 362. In this case the elongation product is treated like the labelled amplificates of this disclosure.

One possible embodiment of a method for the determination of an analyte would work as follows:

i) incubating the target nucleic acid (optionally in excess) with a sample containing the analyte under conditions that allow binding of the target nucleic acid to the analyte, ii) capturing the analyte bound to the target nucleic acid on a solid phase, e.g. by an analyte specific recognition, iii) separating unbound target nucleic acid from the immobilized target nucleic acid, iv) optionally releasing the target nucleic acid from the solid phase, v) incubating the target nucleic acid under the conditions as described for the method for producing multiple copies of nucleic acids as described above (e.g. a primer, a DNA polymerase, dITP and the necessary buffers), subjecting the mixture to temperature cycling to multiply the elongation products, optionally incorporating labels into the elongation products and determining the occurence of the elongation products as described above.

The method of the present invention quantifies an analyte in a sample by first making multiple double-stranded copies, comprising elongation products, of the target nucleic acids which specifically bind the analyte. The sample containing an analyte to be determined is also called a test sample. The amount of analyte in a test sample can be determined from the amount of elongation products determined by the method of the present invention. Methods for quantifying nucleic acids in samples are generally known. The method of the present invention quantifies the elongation products with standardization techniques known in the prior art. A standard curve is generated by using at least two standard samples containing different known amounts of the analyte. The standard samples are subjected to the same method for producing multiple copies of nucleic acids as the test sample and the amounts of elongation products made are determined. It is important that the same conditions, such as reagents, amounts of reagents, temperature and number of steps of elongating primer molecules and separating elongation products, are used in determining the amounts of elongation products made using the standard samples as the test sample.

Based on the quantitative relationship between the amounts of analyte and elongation products determined in the standard samples, the amount of analyte in the test sample can be calculated from the amount of elongation products determined for that test sample. It is preferred that the at least two standard samples be each assayed in duplicate to generate the standard curve. The standard curve is also preferably generated using at least two standard samples with the analyte amount in a standard sample less than the estimated amount of the analyte in the test sample and the analyte amount in another standard sample more than the estimated amount of the analyte in the test sample. More preferably, the standard curve is generated using at least three standard samples each assayed in duplicate.

BRIEF DESCRIPTION OF THE DRAWINGS

FIGS. 5 to 6 show schems of possible reaction routes for 2 modes of the invention, differing in the hybridization site of the primer.

FIGS. 5A and 6A show two embodiments of a process of making multiple copies, of elongation products, E and E', by repeating the steps of elongation, denaturation and hybridization after two identical primers are annealed to the target nucleic acid and an elongation product E.

FIG. 6 shows the second embodiment of the invention, wherein m and n are not equal.

FIG. 8A shows a preferred embodiment of the process of FIG. 6A.

Figure 1A:
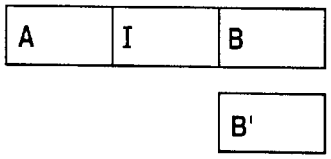
In FIGS. 1A to 1F, several possible arrangements of choosing the analyte specific sequence relative to the target nucleic-acid and the primer are described.

Nothing in the drawings and the description shall be construed to restrict the invention to embodiments wherein only double stranded hybrids are formed. There are some indications that at least under specific conditions triplexes are formed. The formation of triplexes, however, has apparently no negative influence on the products produced or producable according to the present invention.

DETAILED DESCRIPTION OF THE DRAWINGS

In FIG. 1A the hybrid formed from a target nucleic acid containing a separate analyte specific part A, an analyte non-specific template sequence part I and the analyte non-specific sequence B with a primer having the sequence B' which is complementary to sequence B is shown.

Figure 1B:

In FIG. 1B the construct formed from the analyte bound to the target nucleic acid via the analyte specific part of FIG. 1A is shown. It can be seen that in addition the primer containing sequence B' can hybridize to the target nucleic acid.

Figure 1C:
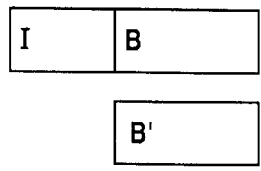

In FIG. 1C a construct formed from a target nucleic acid containing no separate analyte specific part and a primer containing part B' is shown. It can be seen that sequence B is longer than sequence I.

Figure 1D:
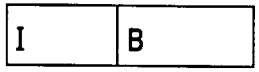

The construct of FIG. 1D can be used to determine an analyte, if the analyte is a nucleic acid and the sequences of I and B are choosen to be complementary to a part of the analyte nucleic acid sequence. In this case, for performing the generation of multiple copies of nucleic acids it may be necessary to denature the hybrid formed from target nucleic acid T and the analyte prior to hybridization of the primer.

Figure 1E:
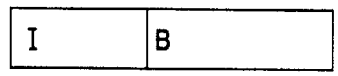

In FIG. 1E the preferred case is shown, wherein the analyte specific pan A is essentially located within and extends over sequence I. Therefore, the primer containing sequence B' could hybridize to the target nucleic acid, but could not be elongated directly. However, if an enzyme having strand displacement activity is used, an elongation can occur.

Figure 1F:
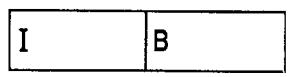

In FIG. 1F a case is shown, wherein the analyte specific part can be attached to I within the sequence I and wherein A is not a nucleic acid sequence but can bind the analyte by for example immunoactive interactions.

Figure 2A:
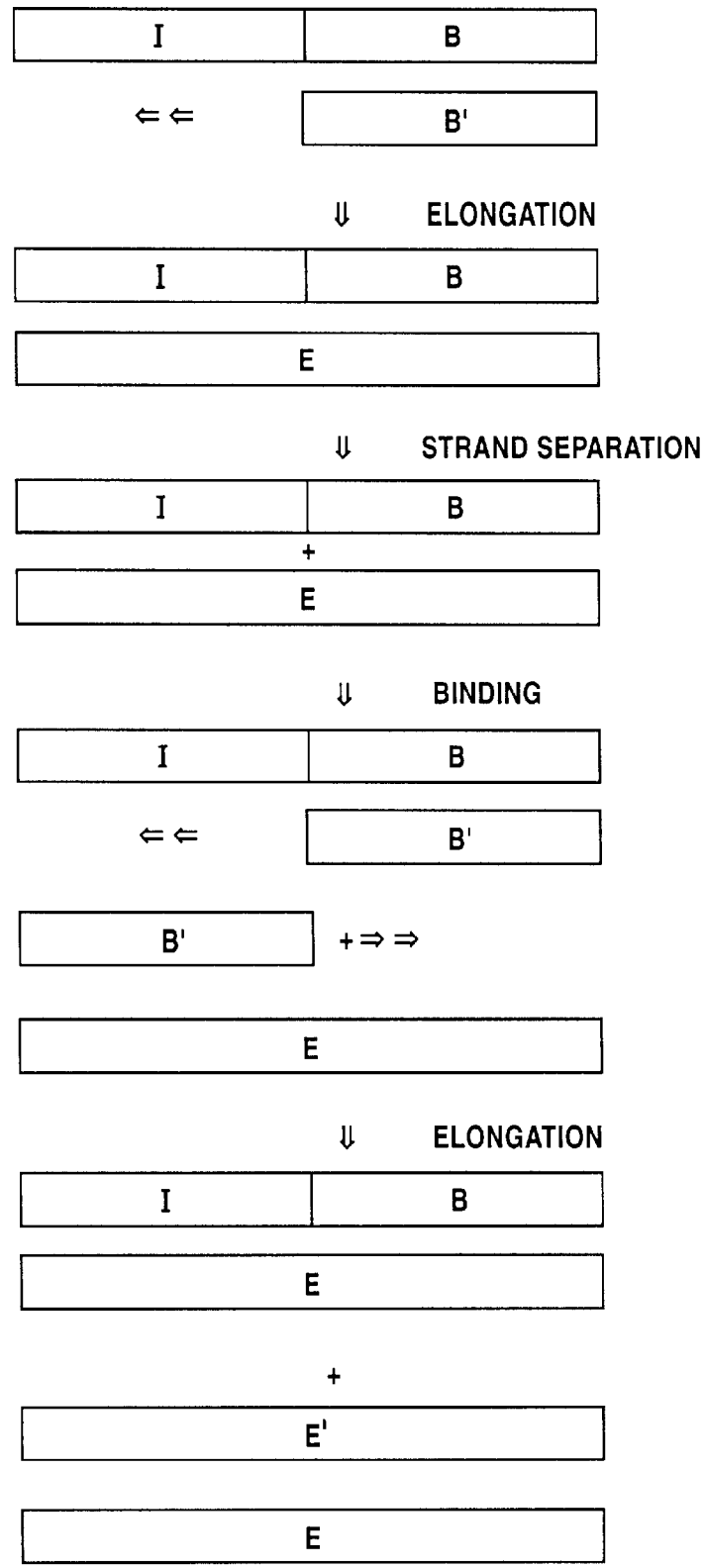
In FIGS. 2A, B and C, possible modes of the reaction are described.

In FIG. 2A, the method of the present invention of generating multiple nucleic acids is shown schematically using a primer substantially consisting of a nucleobase sequence being complementary to the analyte-nonspecific sequence B of the target nucleic acid. Primer B' is elongated to yield the elongation product E. After strand separation to each of the single strands, one molecule of primer can be hybridised and elongated, using either the target nucleic acid or the elongation product E as a template. After strand separation, the newly created extension products E' and the target nucleic acid can again be used as templates in a new round of primer hybridisation, elongation and denaturation and so on.

Figure 2B:
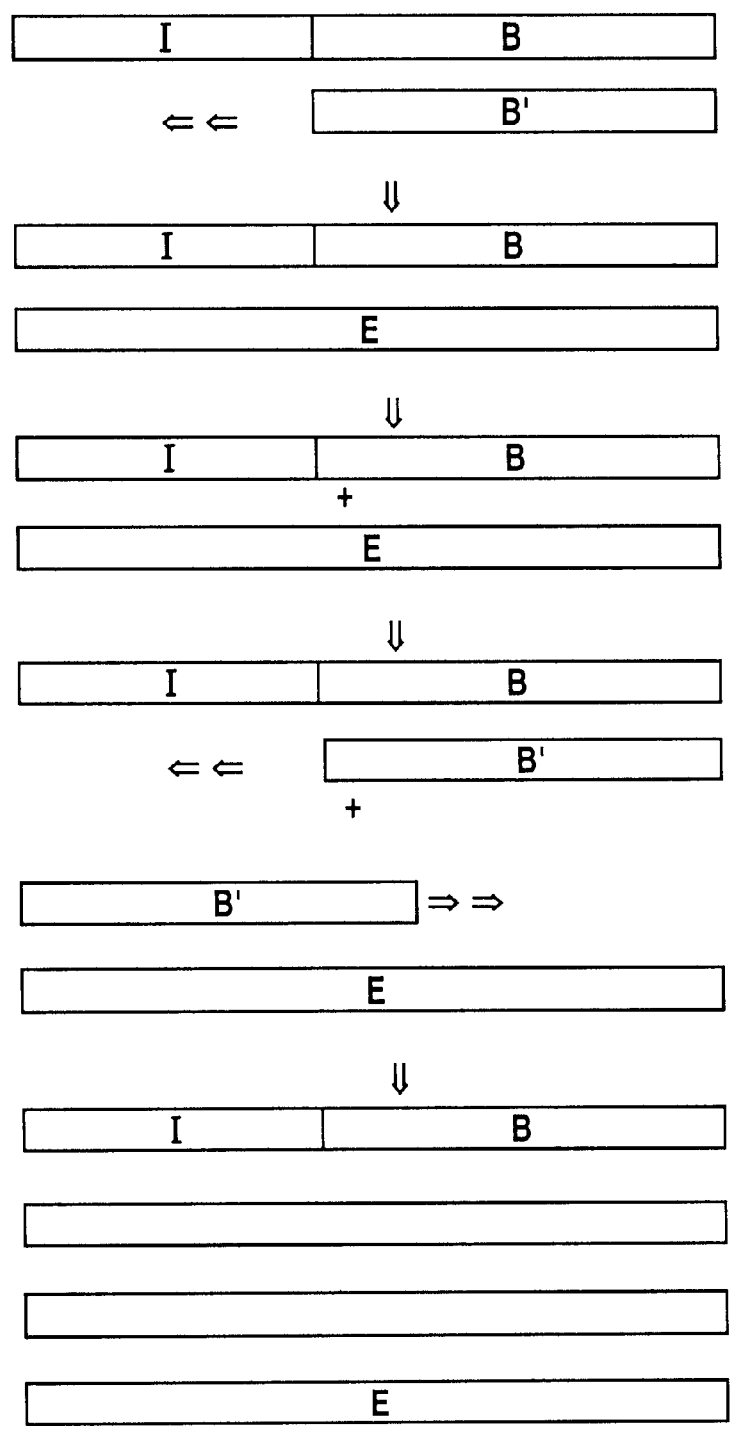

FIG. 2B shows an embodiment comparable to FIGURE. A differing only in that the second primer molecule reaches partly into sequence B when hybridized to any of the elongation products.

Figure 2C:
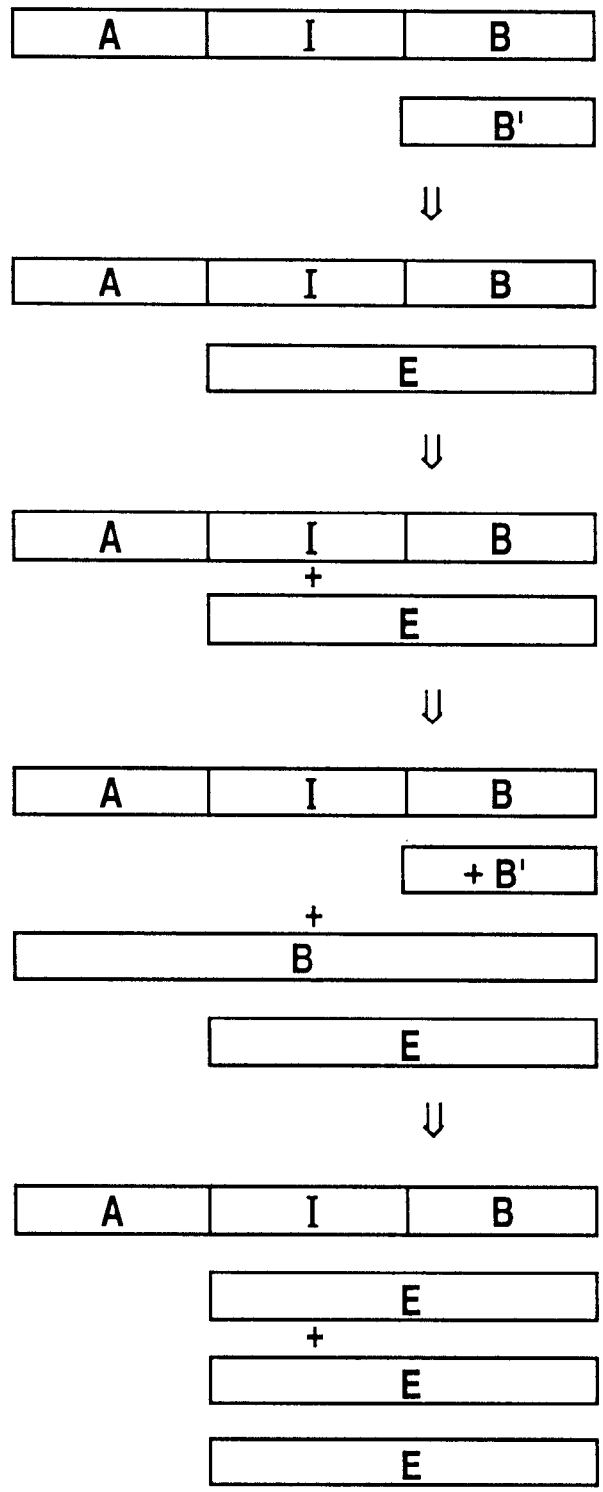

In FIG. 2C the case is shown wherein no elongation of the primer takes place using the analyte-specific region as a template. In this case the primer is hybridised in such a way to the analyte-nonspecific sequence B that it can be elongated using only sequence I as a template for the elongation. The elongation terminates at the end of the analyte-nonspecific part. As shown in FIGS. 2A and 2C. repeated alternate steps of strand separation, hybridisation of additional primer molecules and elongation will generate multiple nucleic acids.

Figure 3:
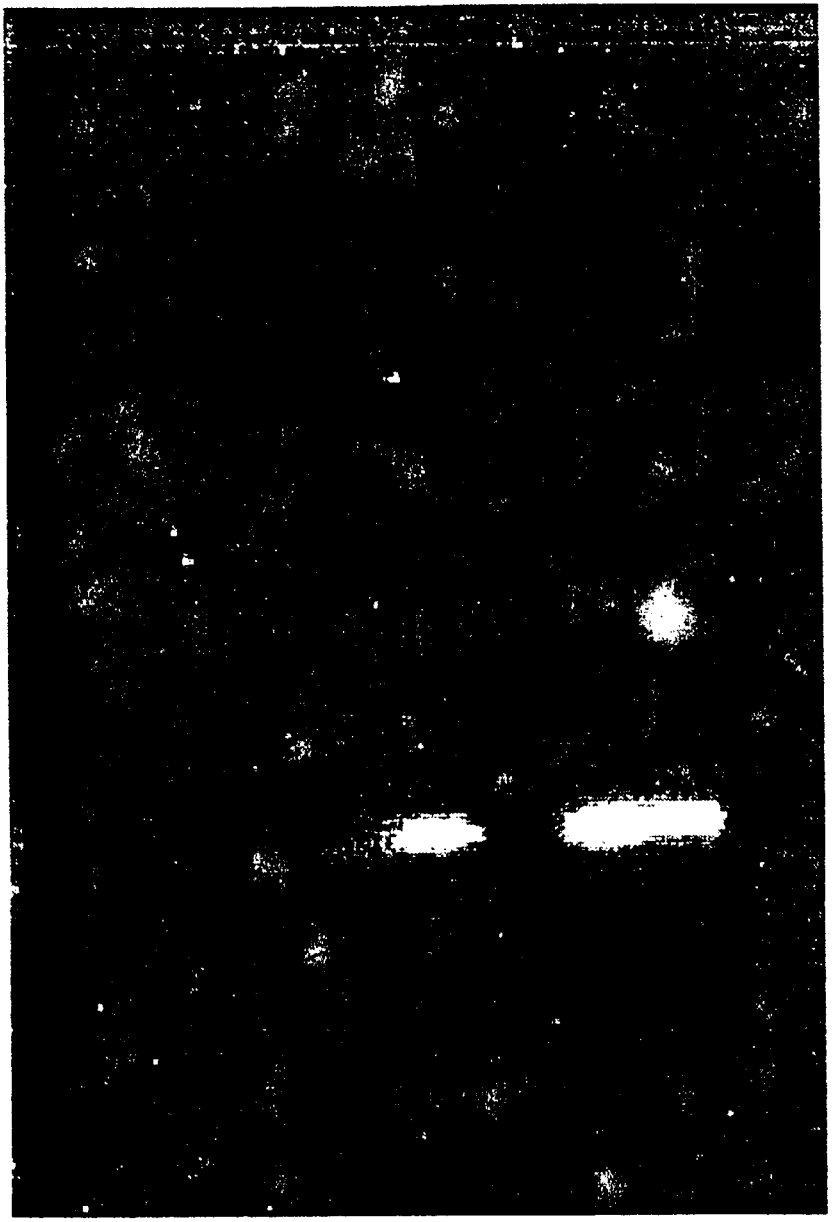
FIG. 3 shows an autoradiogram showing the result of the amplification according to the method of the invention compared to calibration conditions.
Figure 4:
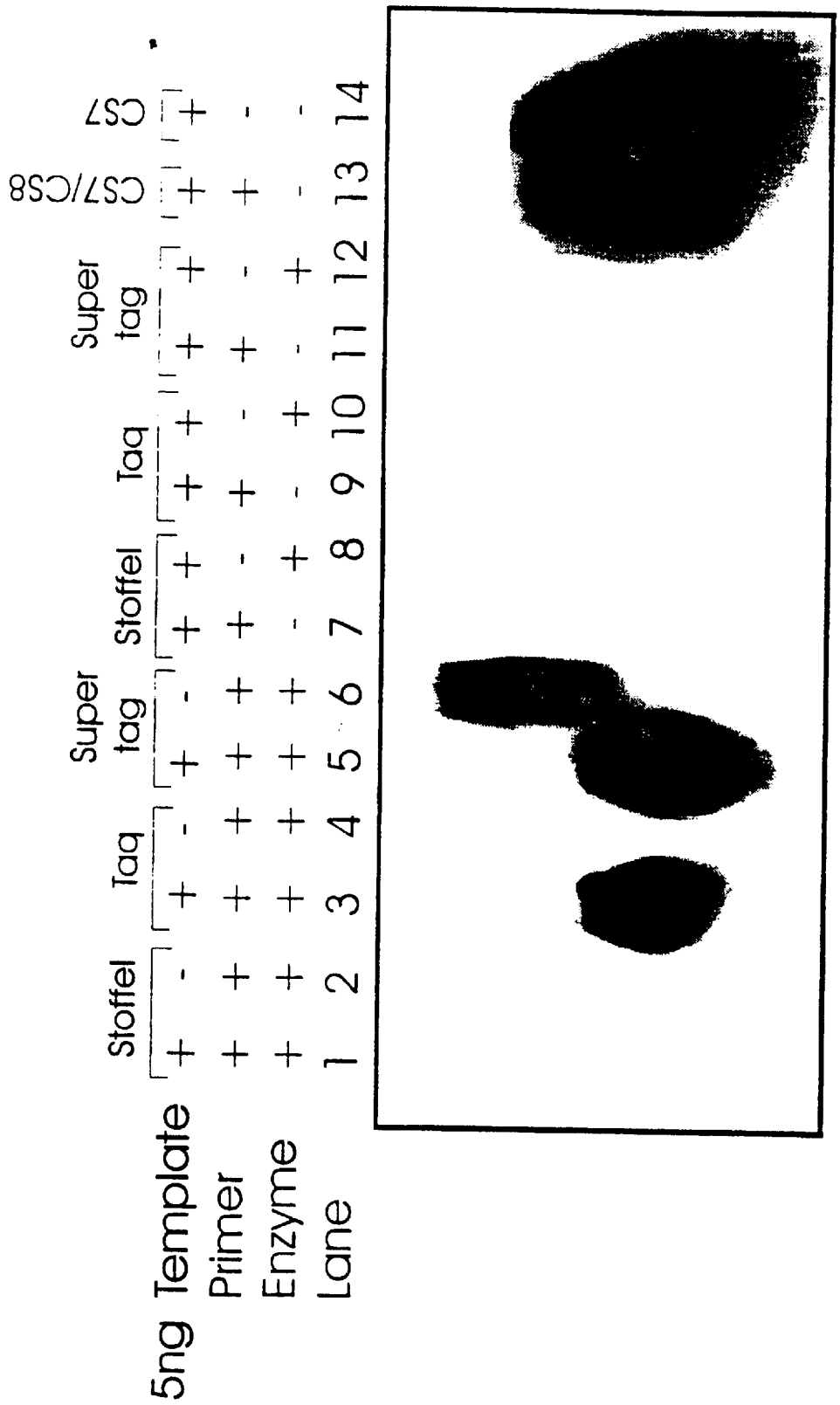
FIG. 4 shows the result of the method using different enzymes.

Detailed descriptions of FIGS. 3 and 4 are found in the examples.

Figure 5:
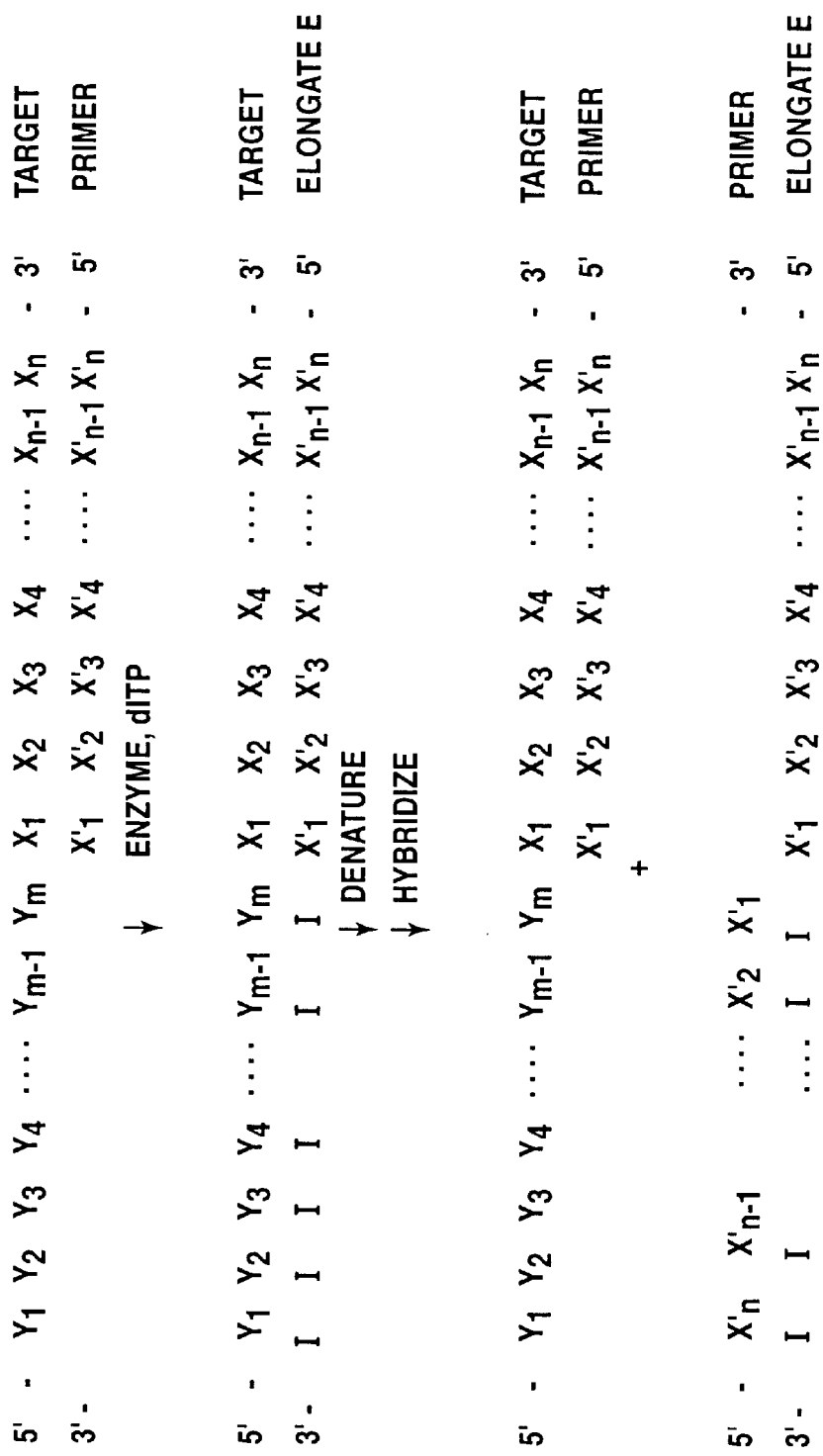

In FIGS. 5 and 6 a general scheme are shown for reactions according to the invention, wherein 2 embodiments can be defined. Y and X are nucleotides. All nucleotides in one line are connected to represent a nucleic acid. The nucleotides specified with a prime(') are complementary to the nucleotides without the prime('). Nucleotides Y are located in segment I, nucleotides X are located in segment B and B' respectively. In all cases m and n are natural numbers being as large as the amount of nucleotides in the section considered.

In a general case the nucleotides Y and X can have any desired meaning, chosing the base moieties from A, G, C, T and U. Under the condition that specific hybridization of the primer with a target is possible, a construct as shown at first in FIGS. 5 and 6 is formed. After elongation with an enzyme and a promiscuous base containing mononucleosidetriphosphate, e.g. dITP, a homoinosine tail is attached to the primer, irrespective of the kind of nucleotides $Y_I \ldots Y_m$. After denaturation one primer can hybridize to the target and one to the elongate E dependent on n, m and the complementary of X and Y. After cycling by elongation, denaturing and hybridization a high number of elongate molecules are formed.

In a simple embodiment the nucleobases in nucleotides $X_I \ldots X_n$ are the same. In this case they can be any base selected from A, G, C. or T or can be a promiscuous base like inosine. In the later case, the nucleotides $X_I' \ldots X_n'$ are preferably cytosine moieties, because the affinity of oligodC to oligodI is high.

The embodiment of FIG. 5 is especially simple when n and m are identical, for example mean 30 each. In this case the primer can hybridize in a specific manner to the stretch of 30 nucleotides (I) attached to the 3'-end of the former primer. If all nucleotides X' have the same meaning, no overlap of hybridization of the second primer with the sequences of the former primer is intended and achieved (FIG. 5). In this case m and n can be the same, for example 30.

In FIG. 6 the case is shown wherein m is $n_{-2}$ and $X_I'$ is complementary to X2'. In this case there is an overlap of the hybridization position of the second primer with the last 2 nucleotides of the former primer. This overlap helps to create a consistence length of elongation products. FIG. 5 shows the general scheme of one embodiment of the present invention.

Figure 7:
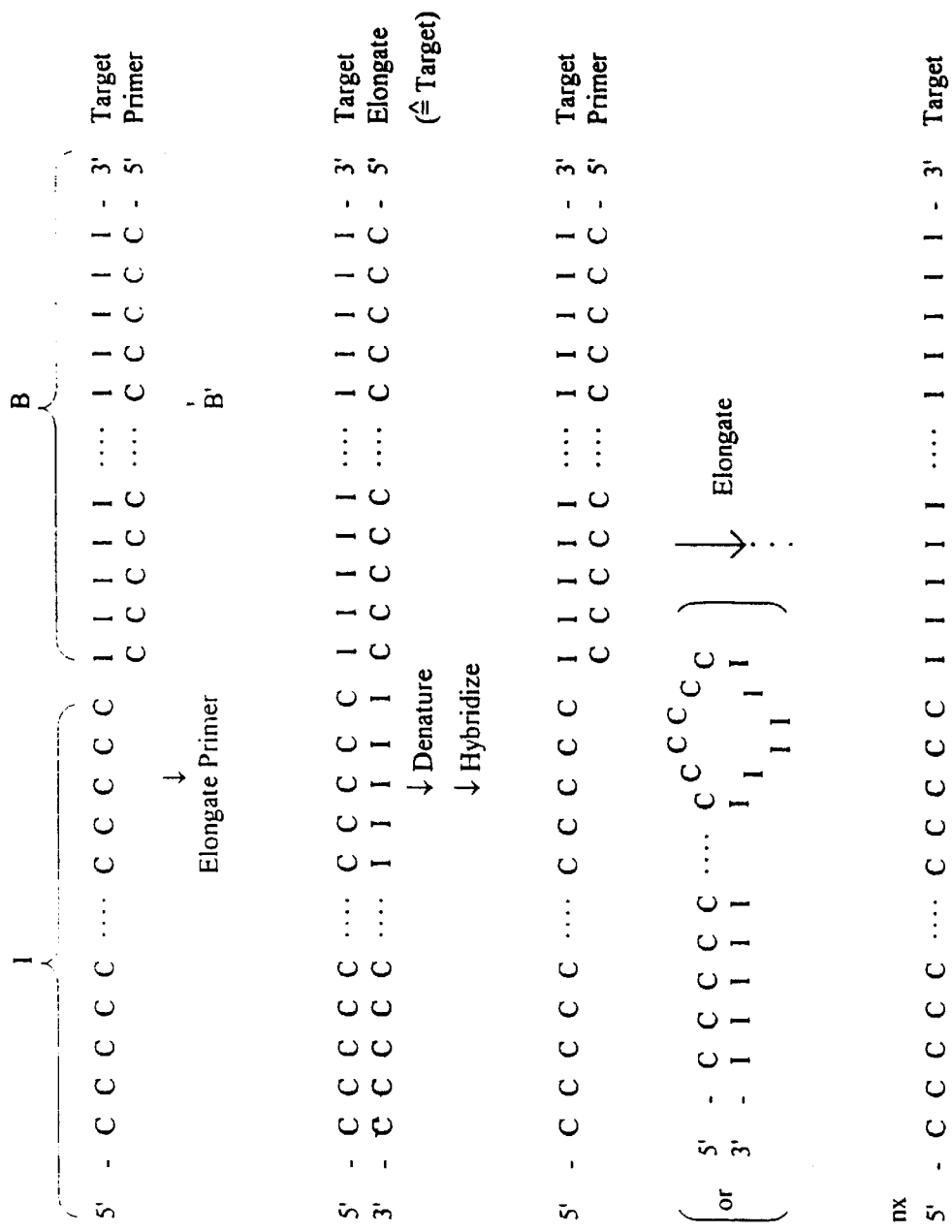
FIG. 7 shows an example of the schematic outline of FIG. 5.

In FIG. 7 the case is shown wherein Y is C, X is I and X' is C and m and n are equal. It can be seen that in this case at first the hybridization position of the primer to the target is not very clearly defined and at the second the possibility to form internal loop structures is increased.

Figure 8:
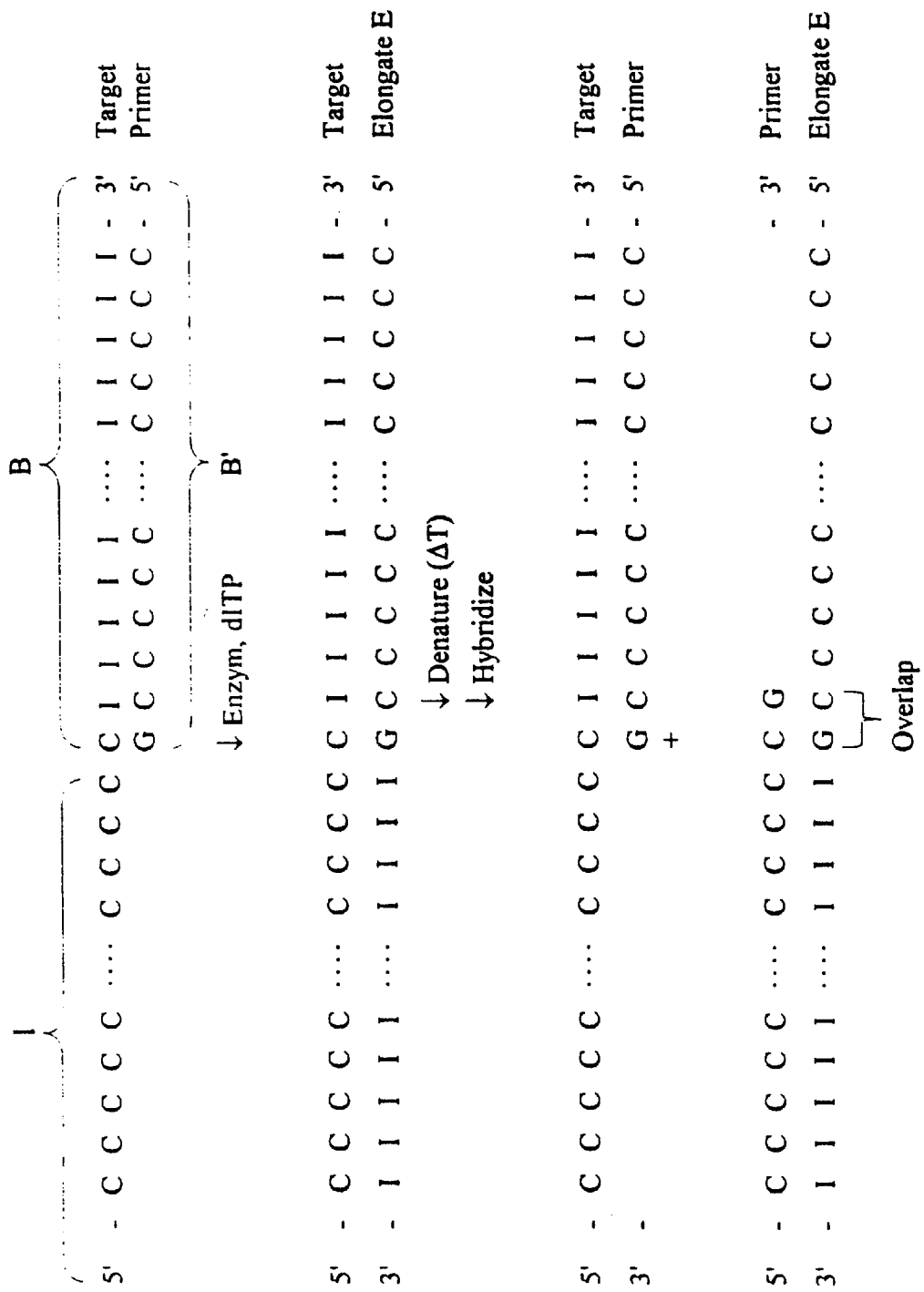
FIG. 8 shows a schematic outline of a specific example of FIG. 6.

Therefore FIG. 8 shows the preferred embodiment, wherein $X'_I$ (e.g. G) is choosen to be complementary to $X_2'$ (e.g. C). This helps to avoid side products of the reaction. FIG. 8 is the schematic drawing of the situation as described in example 2.

The present invention has some considerable advantages. The use of only one primer per target sequence makes this method very simple. In case that only one nucleotide is used, the complexity of the system is even further reduced. In the case where a promiscuous base is used, there is no use for highly thermostable polymerases. In case that only one kind of nucleotide attached is used, the velocity of the process may be increased. The method provides the art with a universally, applicable, sequence independent amplification and short cycle periods.

The present invention can be used in nearly all formats for the determination of analytes. Usually, the generated copies of nucleic acid will be subjected to subsequent determination steps. This might be achieved by the attachment of any label to the nucleic acids generated.

The following examples describe the invention in more detail.

EXAMPLE 1

Synthetic DNA oligonucleotides, 5'-$C_{30}I_{30}$-3'(SEQ ID NO:1), can hybridize to synthetic DNA oligonucleotides, 5'-$C_{30}$-3'(SEQ ID NO:2), 5'-$T_{30}$-3'(SEQ ID NO:3), 5-$C_{30}$G-3' (SEQ ID NO:4) and 5'-$C_{30}$GG-3'(SEQ ID NO:5).

All oligonucleotides were purchased at

DNA Technology APS

Forsherparken/Science Park Aarhus

Gustav Wieds Vej 10

8000, Aarhus C

Denmark

A set of hybridisation reaction (10 μl) were prepared each containing 100 mM NaCl, 10 mM $Na_2HPO_4$, pH 7.0, 0.1 mM EDTA, 0.2 μM of target oligonucleotide (5'-$C_{30}I_{30}$-3') (SEQ ID NO:1) and 0.2 μM of the different oligonucleotides primers shown in FIG. 3. Each reaction was heated to 95° C. for 5 min in a heating block and incubated at room temperature overnight. The next day 2 μl of loading buffer (0.1% bromophenol blue, 0.1% xylene cyanol, 30% glycerol diluted, 0.09M Tris-borate pH 8.3, 1 mM EDTA) was added to each reaction. The samples (10 μl) were then loaded onto a 2% agarose gel and subjected to electrophoresis until the bromophenol blue had migrated to the middle of the gel. The gel was stained with ethidium bromide to visualise the DNA and the gel was photographed. As shown in FIG. 4, the target $C_{30}I_{30}$ oligonucleotide alone (lane 1) does not produce a visible band in the gel. Similarly, no band is apparent in the gel when the hybridisation reactions contain the target $C_{30}I_{30}$ oligonucleotide and either the $I_{30}$ (SEQ ID NO:6) primer (lane 2), the $A_{30}$ (SEQ ID NO:7) primer (lane 3) or the $G_{30}$ (SEQ ID NO:8) primer (lane 6) indicating that these primers do not hybridise to the target oligonucleotide. In contrast, the reactions containing the $C_{30}I_{30}$ template and either the $T_{30}$ primer (lane 4), the $C_{30}$ primer (lane 5), the $C_{30}$G primer (lane 7) or the $C_{30}$GG primer (lane 8) produce a visible band in the gel, indicating that all of these primers hybridise to the template. The finding that only the primers rich in pyrimidine residues hybridise to the template suggests that the observed complex is a triplex consisting of 1 target oligonucleotide and 2 primers. This contention is further supported by the apparent inability of the $I_{30}$ primer to bind to the target sequence.

EXAMPLE 2

Taq Polymerase (Boehringer Mannheim GmbH), Stoffel Fragment (Perkin Elmer) and Super Taq Polymerase can be Used in One Primer, One Nucleotide PCR A set of PCR reactions (50 μl) were prepared as shown in the table. The template is 5'-$C_{30}I_{30}$-3'(SEQ ID NO:1), the primer is 5'-$C_{30}$G-3'(SEQ ID NO:4) and the nucleotide is dITP (Boehriner Mannheim GmbH).

| | 1 | 2 | 3 | 4 | 5 | 6 | 7 | 8 | 9 | 10 | 11 | 12 |
|---|---|---|---|---|---|---|---|---|---|---|---|---|
| Templet (1 ng/μl) | 5 | 0 | 5 | 0 | 5 | 0 | 5 | 5 | 5 | 5 | 5 | 5 |
| Primer(10 μM) | 2 | 2 | 2 | 2 | 2 | 2 | 2 | 0 | 2 | 0 | 2 | 0 |
| 2 mM dITP | 10 | 10 | 10 | 10 | 10 | 10 | 10 | 10 | 10 | 10 | 10 | 10 |
| $H_2O$ | 22 | 27 | 27 | 32 | 27.5 | 32.5 | 23 | 24 | 28 | 29 | 28 | 29.5 |
| 10 × stoffel buffer | 5 | 5 | 0 | 0 | 0 | 0 | 5 | 5 | 0 | 0 | 0 | 0 |
| 25 mM $MgCl_2$ | 5 | 5 | 0 | 0 | 0 | 0 | 5 | 5 | 0 | 0 | 0 | 0 |
| Enzym Stoffel fragment | 1 | 1 | 0 | 0 | 0 | 0 | 0 | 1 | 0 | 0 | 0 | 0 |
| 10 × Boehringer buffer | 0 | 0 | 5 | 5 | 0 | 0 | 0 | 0 | 5 | 5 | 0 | 0 |
| Enzym Boehringer Taq poly | 0 | 0 | 1 | 1 | 0 | 0 | 0 | 0 | 0 | 1 | 0 | 0 |
| 10 × Super Taq buffer | 0 | 0 | 0 | 0 | 5 | 5 | 0 | 0 | 0 | 0 | 5 | 5 |
| Enzym Super Taq | 0 | 0 | 0 | 0 | 1/2 | 1/2 | 0 | 0 | 0 | 0 | 0 | 1/2 |
| | 50 | 50 | 50 | 50 | 50 | 50 | 50 | 50 | 50 | 50 | 50 | 50 |

Enzyme Buffers

10×Taq DNA polymerase buffer from Boehringer Mannheim:

100 mM Tris-HCl, 15 mM $MgCl_2$, 500 mM KCl–pH 8.3 (20° C.)

10×Stoffel fragment buffer:

100 mM Tris-HCl, 100 mM KCl, 30 mM $MgCl_2$–pH 8.3 (20° C.)

10×Super Taq buffer:

500 mM Tris-HCl, 500 mM KCl, 70 mM $MgCl_2$, 160 mM $(NH_4)_2SO_4$–pH 9.0 (25° C.), 0.2 mg/ml BSA The reactions were overlaid with 20 μl of mineral oil and the tubes were placed in a programrnable Thermal Controller Model PTC-100-96V. The PCR cycle was: denaturation at 55° C. for min, annealing at 20° C. for 1 min, synthesis at 37° C. for 2 min and 30 cycles. After amplification each reaction were transferred to an Eppendorf tube and 10 μl of loading buffer (0% bromophenol blue, 0.1% xylene cyanol, 30% glycerol diluted, 0.09M Tris-borate pH 8.3, 1 mM EDTA) was added. The samples (10 μl) were then loaded onto a 2% agarose gel and subjected to electrophoresis along with two size markers. Size marker 1 contained 0.2 μM template (5'-$C_{30}I_{30}$-3'), 0.2 μM primer (5'-$C_{30}$G-3'), 50 mM Tris-HCl, 50 mM KCl, 7 mM $MgCl_2$, 16 mM $(NH_4)_2SO_4$, pH 9.0 (25° C.) and 0.2 mg/ml BSA Size marker 2 (10 μl) contained 0.4 μM template (5'-$C_{30}I_{30}$-3'), 50 mM Tris-HCl, 50 mM KCl, 7 mM $MgCl_2$, 16 mM $(NH_4)_2SO_4$, pH 9.0 (25° C.) and 0.2 mg/ml BSA. Size markers were hybridised at room temperature for 30 min in a 10 μl reaction volume. Before loading on the gel 2 μl loading buffer were added. The gel was electrophoresed until the bromophenol blue had migrated to the middle of the gel. The gel was stained with ethidium bromide to visualise the DNA and photographed. DNA in the gel was transferred to a Gene-Screen+membrane from DuPont using an alkaline transfer buffer (0.4 M NaOH, 0.6 M NaCl). Transfer was made overnight at room temperature. The following day the membrane was neutralised for 10 min in 0.5 M Tris-HCl pH 7.5, 1M NaCl buffer. The membrane was placed in a hybridisation tube and prehybridised in 20 ml hybridisation buffer (0.5 M $Na_2HPO_4$ pH 7.2, 7% SDS, 1 M NaCl) for 2 hours at room temperature in a hybridisation oven. Probe (10 μl of a 1 μM, $^{32}P$ labelled 5'-$C_{30}$G-3' oligonucleotide) was denatured for 5 min at 95° C. and added to the hybridisation tube. Hybridisation was conducted overnight at room temperature. The next day the membrane was washed for 15 †min at room temperature in 200 mM $Na_2HPO_4$—air dried—and subjected to autoradiography. After 6 hours the film was developed.

As shown in FIG. 5, the Taq polymerase from Boehringer Mannheim (lane 3) and the Super Taq polymerase (lane 5) both produce a detectable amplificate of the expected size (compared to the size markers). No signal is detected in the control reactions with the Taq polymerase from Boehringer Mannheim, i.e. when template is omitted (lane 4), when primer is omitted (lane 10) or when the enzyme is omitted from the reaction (lane 9). The Super Taq enzyme also does not produce a detectable amplicon when the primer is omitted (lane 12) and when the enzyme is omitted (lane 11). A weak signal with a location different from the correct amplicon, however, is detected in the control reaction where template is omitted (lane 6). Most likely, this signal is generated by endogenous DNA contaminants present in the Super Taq enzyme acting as template. The Stoffel fragment does not produce a detectable amplicon in the complete reaction (lane 1) or in any of the control reactions without template (lane 2), without primer (lane 8) and without enzyme (lane 7). In conclusion, the Taq polymerase from Boehringer Mannheim and the Super Taq enzyme both catalyse the amplification of the synthetic template using a single primer and a single nucleotide.

We claim:

1. A method for determining an analyte in a sample, comprising
   (a) providing a target nucleic acid comprising a region A, a nucleobase sequence B, and a sequence I linked to the 5' terminus of the nucleobase sequence B, which nucleobase sequence B is not specific for said analyte, wherein said region A specifically binds to said analyte;
   (b) binding said target nucleic acid to said analyte;
   (c) separating the analyte bound to the target nucleic acid from the remaining part of the sample;
   (d) hybridizing a primer to said target nucleic acid, which primer comprises a nucleobase sequence B', wherein the nucleobase sequence B' hybridizes to said nucleobase sequence B;
   (e) elongating the hybridized primer to produce an elongation product E using the target nucleic acid as a template and using nucleotides, wherein at least 30% of said nucleotides contain at least one promiscuous base which is capable of base pairing with each of adenine, guanine, cytosine and thymine;
   (f) separating the target nucleic acid from said elongation product E;
   (g) hybridizing a further primer which comprises the nucleobase sequence B' to said elongation product E, wherein said elongation product E is capable of acting as a template for the elongation of said further primer;
   (h) elongating the hybridized further primer of step (g) to produce an elongation product E' using said elongation product E as a template and using nucleotides, wherein at least 30% of said nucleotides contain at least one said promiscuous base;
   (i) separating said elongation product E from said elongation product E';
   (j) hybridizing a further primer comprising a nucleobase sequence B' to said target nucleic acid or said elongation product E';
   (k) elongating said further primer of step (j) to produce another elongation product E using said target nucleic acid or elongation product E' as a template and using nucleotides, wherein at least 30% of said nucleotides contain at least one said promiscuous base;
   (l) separating said elongation product E of step (k) from said target nucleic acid or elongation product E';
   (m) optionally repeating steps (g)–(l) a sufficient number of times to generate a desired amount of double stranded nucleic acids; and thereafter
   (n) determining said elongation product E and/or elongation product E' as a measure of the presence or amount of said analyte,
   wherein the lengths of the sequence I and the nucleobase sequence B are chosen such that, when said further primer hybridizes to said elongation product E in step (g), said further primer spans a sequence formed by elongation of said hybridized primer of step (e) and overlaps at least a part of the 3' region of said hybridized primer of step (e) by an overlap length.

2. The method of claim 1, wherein at least 80% of said nucleotides in steps (e), (h) and (k) contain at least one promiscuous base.

3. The method of claim 2, wherein 100% of said nucleotides in steps (e), (h) and (k) contain at least one promiscuous base.

4. The method of claim 1, wherein said promiscuous base is inosine or deazainosine.

5. The method of claim 1, wherein said nucleotides are one kind of nucleoside triphosphate.

6. The method of claim 1, wherein the elongation steps are accomplished by the action of at least one enzyme.

7. The method of claim 6, wherein said enzyme is polymerase.

8. The method of claim 7, wherein said polymerase is semithermostable or non-thermostable.

9. The method of claim 1, wherein said analyte is a DNA or RNA.

10. The method of claim 1, further comprising the following step to indirectly label said elongation product E and/or elongation product E' after step (m) and before step (n):
    hybridizing said elongation product E and/or elongation product E' to a labeled nucleic acid probe and then separating hybridized labeled nucleic acid probe from free labeled nucleic acid probe.

11. The method of claim 1, wherein at least one of said nucleotides is labeled to directly label said elongation product E and/or elongation product E', further comprising the following step after step (m) and before step (n):

separating said elongation product E and/or elongation product E' from unincorporated labeled nucleotide molecules.

12. The method of claim 1, wherein the overlap length is not more than 6 nucleotides.

13. The method of claim 12, wherein the overlap length is not more than 4 nucleotides.

14. The method of claim 13, wherein the overlap length is 2 nucleotides.

15. The method of claim 12, wherein at least 80% of said nucleotides in steps (e), (h) and (k) contain at least one promiscuous base.

16. The method of claim 15, wherein 100% of said nucleotides in steps (e), (h) and (k) contain at least one promiscuous base.

17. The method of claim 13, wherein at least 80% of said nucleofides in steps (e), (h) and (k) contain at least one promiscuous base.

18. The method of claim 17, wherein 100% of said nucleotides in step (e) contain at least one promiscuous base.

19. The method of claim 14, wherein at least 80% of said nucleotides in step (e) contain at least one promiscuous base.

20. The method of claim 19, wherein 100% of said nucleotides in step (e) contain at least one promiscuous base.

* * * * *